United States Patent
Katoh et al.

(10) Patent No.: US 8,911,435 B2
(45) Date of Patent: *Dec. 16, 2014

(54) RECANALIZING OCCLUDED VESSELS USING RADIOFREQUENCY ENERGY

(75) Inventors: Osamu Katoh, Nagoya (JP); Wayne Ogata, San Ramon, CA (US)

(73) Assignee: Retrovascular, Inc., Pleasanton, CA (US)

( * ) Notice: Subject to any disclaimer, the term of this patent is extended or adjusted under 35 U.S.C. 154(b) by 1206 days.

This patent is subject to a terminal disclaimer.

(21) Appl. No.: 12/680,500

(22) PCT Filed: Sep. 23, 2008

(86) PCT No.: PCT/US2008/077403
§ 371 (c)(1),
(2), (4) Date: Aug. 3, 2010

(87) PCT Pub. No.: WO2009/042614
PCT Pub. Date: Apr. 2, 2009

(65) Prior Publication Data
US 2010/0292685 A1  Nov. 18, 2010

Related U.S. Application Data

(60) Provisional application No. 60/975,473, filed on Sep. 26, 2007.

(51) Int. Cl.
*A61B 18/18* (2006.01)
*A61B 18/24* (2006.01)

(52) U.S. Cl.
CPC ............ *A61B 18/18* (2013.01); *A61B 18/1815* (2013.01); *A61B 18/245* (2013.01); *A61B 2018/1861* (2013.01)

USPC .................................... 606/34; 606/41

(58) Field of Classification Search
USPC ....................... 606/34, 41; 604/114
See application file for complete search history.

(56) References Cited

U.S. PATENT DOCUMENTS

| | | | |
|---|---|---|---|
| 3,868,956 A | | 3/1975 | Alfidi et al. |
| 5,041,109 A | * | 8/1991 | Abela ............................ 606/15 |
| 5,188,635 A | * | 2/1993 | Radtke ........................... 606/14 |
| 5,366,443 A | | 11/1994 | Eggers et al. |
| 5,419,767 A | | 5/1995 | Eggers et al. |
| 5,501,694 A | | 3/1996 | Ressemann et al. |
| 5,514,128 A | | 5/1996 | Hillsman et al. |
| 5,624,430 A | * | 4/1997 | Eton et al. ......................... 606/1 |

(Continued)

FOREIGN PATENT DOCUMENTS

| | | |
|---|---|---|
| WO | 0009020 | 2/2000 |
| WO | WO2009-042614 | 9/2008 |

OTHER PUBLICATIONS

International Search Report and Written Opinion in International Application No. PCT/US2007/003706, dated Sep. 22, 2008.

(Continued)

*Primary Examiner* — Linda Dvorak
*Assistant Examiner* — Jocelyn D Ram
(74) *Attorney, Agent, or Firm* — LeClairRyan, a Professional Corporation

(57) ABSTRACT

A method and systems for treating chronic total occlusions (CTOs), particularly those that are difficult to treat. CTO recanalization is achieved using radiofrequency ablation directed at the occlusion between antegrade and retrograde guidewires placed on either side of the occlusion.

9 Claims, 6 Drawing Sheets

(56) References Cited

U.S. PATENT DOCUMENTS

| | | | |
|---|---|---|---|
| 5,695,517 A | | 12/1997 | Marin et al. |
| 5,851,185 A | * | 12/1998 | Berns .................... 600/434 |
| 5,895,398 A | | 4/1999 | Wensel et al. |
| 6,068,645 A | * | 5/2000 | Tu ........................ 606/200 |
| 6,068,688 A | | 5/2000 | Tu et al. |
| 6,235,044 B1 | | 5/2001 | Root et al. |
| 6,416,523 B1 | | 7/2002 | Lafontaine |
| 6,454,775 B1 | * | 9/2002 | Demarais et al. ......... 606/128 |
| 6,697,863 B1 | | 2/2004 | Egawa |
| 6,911,026 B1 | | 6/2005 | Hall et al. |
| 6,936,056 B2 | | 8/2005 | Nash et al. |
| 7,037,316 B2 | | 5/2006 | McGuckin et al. |
| 8,545,418 B2 | * | 10/2013 | Heuser .................... 600/585 |
| 2003/0028200 A1 | * | 2/2003 | Berg et al. ................ 606/108 |
| 2003/0065316 A1 | * | 4/2003 | Levine et al. ............. 606/33 |
| 2004/0082962 A1 | * | 4/2004 | Demarais et al. ......... 606/128 |
| 2004/0230219 A1 | | 11/2004 | Roucher, Jr. et al. |
| 2005/0154400 A1 | | 7/2005 | Kato et al. |
| 2005/0171478 A1 | | 8/2005 | Selmon et al. |
| 2006/0079880 A1 | | 4/2006 | Sage et al. |
| 2006/0224112 A1 | | 10/2006 | Lentz |
| 2007/0043389 A1 | | 2/2007 | Shindelman |
| 2007/0049867 A1 | | 3/2007 | Shindelman |
| 2007/0112342 A1 | * | 5/2007 | Pearson et al. ............ 606/34 |
| 2007/0173878 A1 | * | 7/2007 | Heuser .................... 606/185 |
| 2007/0208368 A1 | | 9/2007 | Katoh et al. |
| 2007/0293846 A1 | * | 12/2007 | von Oepen et al. ........ 604/529 |
| 2008/0039830 A1 | * | 2/2008 | Munger et al. ............ 606/33 |
| 2008/0039935 A1 | | 2/2008 | Buch et al. |
| 2008/0154153 A1 | * | 6/2008 | Heuser .................... 600/585 |
| 2008/0306499 A1 | | 12/2008 | Katoh et al. |
| 2008/0312673 A1 | * | 12/2008 | Viswanathan et al. ..... 606/159 |
| 2010/0256616 A1 | | 10/2010 | Katoh et al. |
| 2010/0292685 A1 | | 11/2010 | Katoh et al. |
| 2013/0072957 A1 | * | 3/2013 | Anderson ............... 606/194 |

OTHER PUBLICATIONS

International Search Report and Written Opinion in International Application No. PCT/US2008/077403, dated Dec. 1, 2008.
International Search Report and Written Opinion in International Application No. PCT/US2009/041287, dated Jul. 7, 2009.
Office Action in U.S. Appl. No. 12/150,111, mailed Nov. 18, 2010.
Office Action in U.S. Appl. No. 11/706,041, mailed May 12, 2010.
Notice of Allowance in U.S. Appl. No. 11/706,041, mailed Nov. 26, 2010.
Office Action in U.S. Appl. No. 12/150,111, mailed Apr. 22, 2011.
Canadian Office Action in Canadian Application No. 2,641,729, dated May 14, 2010.
Australian Office Action in Australian Application No. 2007215224, dated Apr. 8, 2010.
Bourassa, Martial G. et al., "Bypass Angioplasty Revascularization Investigation: Patient Screening, Selection, and Recruitment," The American Journal of Cardiology, vol. 75, Issue 9, pp. 3C-8C, 1995.
Colombo, Antonio et al., "Treating Chronic Total Occlusions Using Subintimal Tracking and Reentry: The STAR Technique," Catheterization and Cardiovascular Interventions, vol. 64, No. 4, pp. 407-411, 2005.
Ito, Shigenori et al., "Novel Technique Using Intravascular Ultrasound-Guided Guidewire Cross in Coronary Intervention for Uncrossable Chronic Total Occlusions," Circulation Journal, vol. 68, No. 11, pp. 1088-1092, Nov. 2004.
Kimura, Bruce J. et al., "Subintimal Wire Position During Angioplasty of a Chronic Total Coronary Occlusion: Detection and Subsequent Procedural Guidance by Intravascular Ultrasound," Catheterization and Cardiovascular Diagnosis, vol. 35, No. 3, pp. 262-265, 1995.
King, Spencer B. et al., "A Randomized Trial Comparing Coronary Angioplasty with Coronary Bypass Surgery," The New England Journal of Medicine, vol. 331, No. 16, pp. 1044-1050, Oct. 20, 1994.
Kinoshita, Isao et al., "Coronary Angioplasty of Chronic Total Occlusions With Bridging Collateral Vessels: Immediate and Follow-Up Outcome From a Large Single-Center Experience," Journal of the American College of Cardiology, vol. 26, No. 2, pp. 409-415, Aug. 1995.
Matsubara, Tetsuo et al., "IVUS-Guided Wiring Technique: Promising Approach for the Chronic Total Occlusion," Catheterization and Cardiovascular Interventions, vol. 61, No. 3, pp. 381-386, 2004.
Melchior, Jean-Paul et al., "Improvement of Left Ventricular Contraction and Relaxation Synchronism After Recanalization of Chronic Total Coronary Occlusion by Angioplasty," Journal of the American College of Cardiology, vol. 9, No. 4, pp. 763-768, Apr. 1987.
Olivari, Zoran et al., "Immediate Results and One-Year Clinical Outcome After Percutaneous Coronary Interventions in Chronic Total Occlusions: Data From a Multicenter, Prospective, Observational Study (TOAST-GISE)," Journal of the American College of Cardiology, vol. 41, No. 10, pp. 1672-1678, 2003.
Suero, James A. et al., "Procedural Outcomes and Long-Term Survival Among Patients Undergoing Percutaneous Coronary Intervention of a Chronic Total Occlusion in Native Coronary Arteries: A 20-Year Experience," Journal of the American College of Cardiology, vol. 38, No. 2, pp. 409-414, 2001.
Bolia, A. et al. "Recanalization of Iliac Artery Occlusion by Subintimal Dissection Using the Ipsilateral and the Contralateral Approach," Clinical Radiology, vol. 52, pp. 684-687, 1997.
Spinosa, David J. et al. "Simultaneous Antegrade and Retrograde Access for Subintimal Recanalization of Peripheral Arterial Occlusion," Journal of Vascular and Interventional Radiology, vol. 14, Issue 11, pp. 1449-1454, Nov. 2003.
Australian Office Action in Australian Application No. 2008304599, dated Feb. 22, 2011.
Korean Non-Final Rejection for Korean Application No. 10-2008-7022167, dated Nov. 23, 2010.
Feb. 22, 2011 Examination Report issued on Australian Patent Application No. 2008304599 issued by the Australian Patent Office, pp. 1-4
Jul. 20, 2012 Filed Response to Feb. 22, 2011 Examination Report issued on Australian Patent Application No. 2008304599, pp. 1-20.
Sep. 20, 2012 Examination Report issued on Australian Patent Application No. 2008304599 issued by the Australian Patent Office, pp. 1-4.
Oct. 11, 2012 Filed Response to Sep. 4, 2012 Second Examination Report issued on Australian Patent Application Serial No. 208304599, pp. 1-7.
Mar. 1, 2012 Examination Report issued on Australian Patent Application No. 2009239406 issued by the Australian Patent Office, pp. 1-2 Abandoned.
May 25, 2012 Office Action issued by Canadian Patent Office on Canadian Patent Application No. 2,722,486, pp. 1-3.
Nov. 23, 2012 Filed Response to May 25, 2012 Office Action issued by Canadian Patent Office on Canadian Patent Application No. 2,722,486, pp. 1-4.
May 14, 2010 Office Action issued by Canadian Patent Office on Canadian Patent Application No. 2,641,729, pp. 1-3.
Nov. 15, 2010 Filed Response to May 14, Official Action issued by Canadian Patent Office on Canadian Patent Application No. 2,641,729, pp. 1-13.
Feb. 28, 2011 Office Action issued by Canadian Patent Office on Canadian Patent Application Canadian Patent Application 2,641,729, pp. 1-3.
Aug. 22, 211 Filed Response to Feb. 28, 2011 Official Action issued by Canadian Patent Office on Canadian Patent Application No. 2,641,729, pp. 1-24.
Jan. 12, 2012 Office Action issued by Canadian Patent Office on Canadian Patent Application No. 2,641,729, pp. 1-3.
Jul. 11, 2012 Filed Response to Jan. 12, 2012 Official Action issued by Canadian Patent Office on Canadian Patent Application No. 2,641,729, pp. 1-9.
Jul. 24, 2012 Extended Supplementary European Search Report, issued by the European Patent Office for European patent application serial No. 08834456.9, pp. 1-9.
Nov. 19, 2012 Filed Response to Jul. 24, 2012 Extended Supplementary European Search Report, issued by the European Patent Office for European patent application serial No. 08834456.9, pp. 1-10.

(56) References Cited

OTHER PUBLICATIONS

Feb. 24, 2011 Supplementary European Search Report, issued by the European Patent Office for European patent application serial No. 09734649.8, pp. 1-6.
Sep. 26, 2011 Filed Response to Feb. 24, 2011 Search Opinion issued by the European Patent Office for European patent application serial No. 09734649.8, pp. 1-8.
Nov. 23, 2011 Examination Report issued by the European Patent Office for European patent application serial No. 09734649.8, pp. 1-3.
Feb. 7, 2012 European Associate's Comments in reply to Communication Pursuant to Article 94(3) issued by the European Patent Office for European patent application serial No. 09734649.8, pp. 1-2.
Jun. 4, 2012 Filed Response to Nov. 23, 2011 Examination Report issued by the European Patent Office for European patent application serial No. 09734649.8, pp. 1-4.
Dec. 10, 2012 Decision to Refuse European Application issued by the European Patent Office for European patent application serial No. 09734649.8, pp. 1-8.
May 31, 2011 Office Action issued by Japanese Patent Office on Japanese Patent Application No. 2008-554416, pp. 1-4.
Jul. 26, 2011 Filed Response on May 31, 2011 Office Action issued by Japanese Patent Office on Japanese Patent Application No. 2008-554416, pp. 1-3.
Mar. 28, 2012 Certificate of Patent issued Feb. 24, 2012 by Japanese Patent Office on Japanese Patent Application No. 2008-554416, pp. 1-3.
Jun. 15, 2012 Notice of Reason for Rejection issued by Japanese Patent Office on Japanese Patent Application No. 2011-506400, pp. 1-7.
Sep. 17, 2012 Instructions for Response to Jun. 15, 2012 Notice of Reason for Rejection (Decision of Rejection) issued by Japanese Patent Office on Japanese Patent Application No. 2011-506400, pp. 1-12.
Nov. 6, 2012 Decision of Rejection issued by Japances Patent Office on Japanese Patent Application 2011-506400, pp. 1-3.
Dec. 27, 2012 Foreign Associates Comments on Nov. 6, 2012 Decision of Rejection issued by Japanese Patent Office on Japanese Patent Application No. 2011-506400, pp. 1-6.
Nov. 23, 2010 Non-Final Rejection issued by Korean Patent Office on Korean Application No. 10-2008-7022167 pp. 1-8.
Jan. 24, 2011 Filed Response to Nov. 23, 2010 Non-Final Rejection issued by Korean Patent Office on Korean Application No. 10-2008-7022167 pp. 1-26
Jul. 20, 2011 Notice of Allowance issued by Korean Patent Office on Korean Application No. 10-2008-7022167 pp. 1-3.
May 18, 2012 Instructions for Response to Dec. 19, 2011 Non-Final Rejection issued by Korean Patent Office on Korean Application No. 10-2010-7008803 pp. 1-5.
Oct. 29, 2012 Notice of Allowance issued by Korean Patent Office on Korean Application No. 10-2010-7008803 pp. 1-3.
Sep. 22, 2008 International Search Report for PCT/US2007/03706, pp. 1-2.
Oct. 21, 2008 International Preliminary Report on Patentability with Written Opinion issued on PCT Application No. PCT/US2007/003706, pp. 1-4.
Dec. 1, 2008 International Search Report issued for PCT Application No. PCT/US2008/077403, p. 1.
Jul. 7, 2009 International Search Report Issued for PCT Application No. PCT/US2009/041287, pp. 1-2.
Jun. 14, 2011 International Search Report and Written Application issued on PCT Application No. PCT/US2011/031018, pp. 1-7.
Apr. 22, 2011 Final Office Action for U.S. Appl. No. 12/150,111, pp. 1-8.
Jul. 22, 2011 Filed Response to Apr. 22, 2011 Final Office for U.S. Appl. No. 12/150,111, pp. 1-9 with RCE.
Feb. 13, 2013 Office Action for U.S. Appl. No. 12/753,844, pp. 1-15.
Feb. 4, 2013 Office Action for U.S. Appl. No. 13/037,304, pp. 1-15.

* cited by examiner

RECANALIZING OCCLUDED VESSELS USING RADIOFREQUENCY ENERGY

CROSS REFERENCE TO RELATED APPLICATIONS OR PRIORITY CLAIM

This application is a national stage application under 35 U.S.C. §371 from PCT Application No. PCT/US2008/077403, filed Sep. 23, 2008, which claims the priority benefit of U.S. Provisional Application No. 60/975,473, filed Sep. 26, 2007.

FIELD OF THE INVENTION

This invention relates generally to dealing with occlusions of the lumen and more specifically to apparatus and methods for crossing severe or total chronic occlusions of lumens in the body using radiofrequency energy.

DESCRIPTION OF THE RELATED ART

Chronic total occlusion (CTO) is the complete blockage of a vessel and usually has serious consequences if not treated in a timely fashion. The blockage could be due to atheromatous plaque or old thrombus. One of the common procedures for treating CTOs of the coronary arteries is percutaneous transluminal coronary angioplasty (PTCA). During a PTCA procedure, a small incision is, typically, made in the groin. A guiding catheter over a guide wire is introduced into the femoral artery and advanced to the occlusion. Frequently, with gentle maneuvering, the guidewire is able to cross the occlusion. Then, a balloon-tipped angioplasty catheter is advanced over the guide wire to the occlusion. The balloon is inflated, separating or fracturing the atheroma. Some of the common steps involved in the PTCA procedure are the simultaneous injection of a contrast agent in the contra-lateral vessel, getting backup force or stabilization for a guide wire (which could invoke additional personnel to handle the catheter), puncturing the plaque, drilling or rotating the guide wire to push it through the dense plaque, etc. Because of the stiff resistance sometimes offered by dense plaque, one could be forced to use stiff wires. Occasionally, the wires could puncture the vessel wall calling for remedial measures.

The most common percutaneous coronary intervention (PCI) failure mode for CTOs is inability to successfully pass a guidewire across the lesion into the true lumen of the distal vessel. To date, there is no consensus on how best to treat CTO after attempts with conventional guidewires have failed. Different strategies and specific devices for CTOs have been developed including the subintimal tracking and reentry with side branch technique, parallel wire technique, IVUS guided technique, retrograde approach, etc.

Mechanical and energy based techniques have also been proposed for passing guidewires through hard calcified occlusions, such as mechanical cutting or oscillation and laser or ultrasound or radiofrequency (RF) energy ablation. Most of these devices work by locally applying energy at the tip of the guidewire or catheter device to cause ablation of the occlusion, which is carefully carried out to create a channel through the occlusion. Once a channel is created, the guidewire is used to guide the balloon catheter in place.

RF energy is widely used to coagulate, cut or ablate tissue. In both modalities, monopolar and bipolar, conductive electrodes contact the tissue to be treated. In the monopolar mode, the active electrode is placed in contact with the tissue to be treated and a return electrode with a large surface area is located on the patient at a distance from the active electrode. In the bipolar mode, the active and return electrodes are in close proximity to each other bracketing the tissue to be treated. Sometimes an array of electrodes is used to provide better control over the depth of penetration of the RF field and hence control over the temperatures to which the tissue is heated. There are many disadvantages with each mode. For example, in the monopolar arrangement, because of the large physical separation between the electrodes there are frequent reports of local burning at the electrode sites. This would clearly be undesirable where one of the electrodes will be inside a blood vessel. The other serious issue is the likelihood of forming blood clots. The tissue that is in contact with the electrodes can be coagulated or ablated. In the case of the electrodes being present inside a blood vessel the chances of forming dangerous blood clots is quite high.

In an attempt to overcome the issues described above, various device and electrode configurations are described in the following patents. U.S. Pat. Nos. 5,366,443 and 5,419,767 describe the use of RF electrodes on a catheter to cross a lesion. These patents describe a bipolar electrode assembly at the distal tip of a catheter that is in contact with the occlusion, and patentees claim that application of RF energy ablates the occlusion and renders the occlusion susceptible for the guidewire to penetrate. This method has the drawback that careful tracking of the occlusion and the ablation process is necessary to avoid trauma to the vessel walls or healthy tissue, since the possibility of short-circuiting of current through healthy tissue instead of the occlusion is high. U.S. Pat. No. 5,419,767 overcomes this limitation to a certain extent through the use of a multiple electrode array. However, this device requires a channel to be pre-created through the occlusion so that the device can be passed through a guidewire traversing this channel, which is not always easy.

U.S. Pat. No. 5,514,128 to Hillsman et al. describes a laser catheter device that enables ablation of an occlusion in the vasculature. This system has similar drawbacks to the ones described above—need for a guidance system, potential for healthy tissue to be ablated, complexity (and hence cost) of the device, etc.

One major problem with the existing devices is the potential for the ablation energy to damage the walls of the vasculature, in the absence of a mechanism to track the orientation and position of the energy delivery member. Several devices exist in the prior art that address the issue of tracking and steering of the energy delivery element. U.S. Pat. No. 6,911,026 to Hall et al. describes a magnetic steering and guidance system to direct an ablation device that delivers RF energy at the tip in a unipolar configuration where the return electrode is placed externally in contact with the body or in a bipolar configuration where the return electrode is a ring surrounding the central wire electrode.

U.S. Pat. No. 6,416,523 to Lafontaine discusses a mechanical cutting device where the guidance is provided by measuring impedance of the tissue in contact. The guidance system senses the difference in impedance between the stenotic tissue and the vessel wall and directs the cutting element to the occlusion.

However, none of these alternate strategies have provided satisfactory results for the most challenging of the CTOs. In case of hard calcified occlusions, the revascularization procedure can be tedious and time consuming. Therefore, there is a need for improved methods of ablating or disrupting the occlusive material that are safe, efficacious and fast. It would be beneficial to have alternate techniques and devices that would recanalize a CTO without the shortcomings of the current techniques.

CTOs that are hard to recanalize, either because of the tortuous anatomy of the diseased vessel, or because the proximal end of the stenosis is too hard for the guide wire to penetrate, or other characteristics of the CTO that would make the standard procedure vulnerable to failure would benefit from newer approaches to recanalize CTOs. Recently a combined antegrade-retrograde approach has been proposed for recanalizing chronic occlusions (U.S. application Ser. No. 11/706,041). The method disclosed in the co-pending application would benefit from the use of energy for crossing CTOs.

SUMMARY OF THE INVENTION

Various methods and devices are provided to overcome some of the commonly encountered problems in treating chronic total occlusions. One aspect of this invention is to provide a method and systems for successfully recanalizing an occluded vessel by advancing, in combination, guidewires in an antegrade and retrograde fashion to the occlusion and applying RF energy between the proximal and distal ends of the occlusion. The RF energy application across the occlusion is accomplished using a bipolar arrangement, where one electrode is located on the antegrade guidewire and the other electrode that makes up the bipolar arrangement is located on the retrograde guidewire.

In one aspect, the present invention discloses a method of recanalizing an occluded vessel comprising advancing in an antegrade fashion a first longitudinal member through a proximal end of an occlusion, advancing in a retrograde fashion a second longitudinal member through a distal end of the occlusion, applying RF energy between the distal ends of the antegrade and retrograde guidewires, ablating the tissue locally, and creating a channel through which a guidewire could be advanced. In another embodiment, the retrograde guidewire could have a deployable capture mechanism at its distal end and upon deployment could snare the antegrade guidewire.

In another aspect, this invention relates to a catheter assembly for recanalizing an occluded vessel comprising an antegrade longitudinal member with a distal end containing an RF electrode and a retrograde longitudinal member with a distal end containing a second RF electrode; and the proximal end of the catheter assembly connected to an RF generator. Additionally, a temperature measuring element could be disposed on the distal ends of the antegrade or retrograde longitudinal member. The RF generator could also be programmed to treat the tissue for a pre-set time or until a set condition has been reached. One such condition could be till the occlusion has reached a pre-determined temperature. Another condition could be the impedance of the occlusion.

In another aspect, the invention is a kit for recanalizing occluded vessels comprising one or more of the following: an antegrade guidewire, a retrograde guidewire, a dilating device, a capture device and an injection catheter, wherein at least one of these devices contains at least one electrode. Additionally, the proximal ends of this device are configured to be coupled with an RF generator.

Other aspects of the invention include methods corresponding to the devices and systems described above.

BRIEF DESCRIPTION OF THE DRAWINGS

The invention has other advantages and features which will be more readily apparent from the following detailed description of the invention and the appended claims, when taken in conjunction with the accompanying drawings, in which:

DETAILED DESCRIPTION

Figure 1:
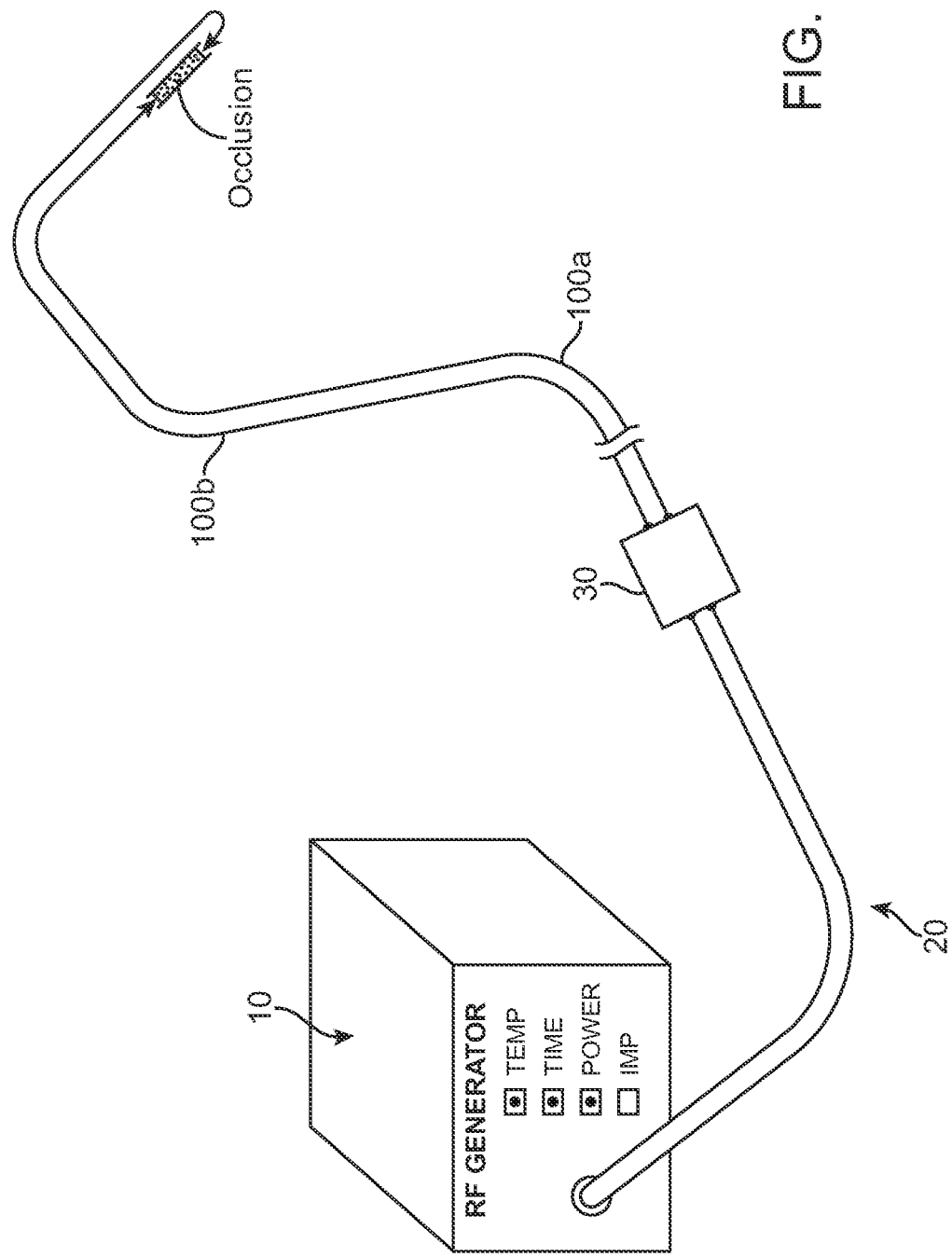
FIG. 1 is a schematic showing an RF generator connected to the longitudinal members.

Although the detailed description contains many specifics, these should not be construed as limiting the scope of the invention but merely as illustrating different examples and aspects of the invention. It should be appreciated that the scope of the invention includes other embodiments not discussed in detail above. Various other modifications, changes and variations which will be apparent to those skilled in the art may be made in the arrangement, operation and details of the method and apparatus of the present invention disclosed herein without departing from the spirit and scope of the invention as described here.

The present embodiments combine the use of RF energy delivered through antegrade and retrograde members for recanalizing occluded lumens, particularly chronic total occlusions. The methods and systems described herein recanalize difficult to cross occlusions by taking advantage of an antegrade and retrograde approach to establish a bipolar electrode arrangement across the occlusion. This approach minimizes the potential of the vessel wall becoming perforated or injured, as may otherwise occur in a conventional bipolar RF treatment approach, where both RF electrodes are on the same side of the occlusion. Because the electrodes are distributed on opposite sides of the occlusion, the tissue that is ablated by the RF treatment (i.e., the occlusion) is well contained between the electrodes. This also allows the user to localize the treatment to the occlusion.

As disclosed in the co-pending U.S. patent application Ser. No. 11/706,041 by the same inventors, which is incorporated herein in its entirety, in the controlled antegrade and retrograde tracking (CART) technique the retrograde approach takes advantage of an intercoronary channel. Such a channel may be an epicardial channel, an inter-atrial channel, an intra-septal channel (also referred to as septal collateral), or a bypass graft. The basic concept of the CART technique is to create a channel through an occlusion, preferably with limited dissections, by approaching the occlusion both antegradely and retrogradely.

While the combined antegrade and retrograde approach has been effective in crossing difficult to cross lesions, it has been observed that using energy, for example RF energy, to ablate or alter the tissue in a controlled fashion is beneficial in crossing hard to cross lesions. Such controlled energy deployment is achieved using a bipolar arrangement of the electrodes, where one electrode is located on the antegrade element and the other electrode that constitutes the bipolar arrangement is located on the retrograde element. These electrodes can also be referred to as the return and active electrodes. They are also referred to as the anode and cathode, respectively. The electrodes could also be arranged in an array (multiple electrodes), where the electrode arrangement provides better control over the depth of penetration of the RF field and thereby provides the ability to control the tissue temperature.

FIG. 1 shows a system for recanalizing occluded vessels using RF energy. The system comprises longitudinal members 100a and 100b for delivering RF energy to an occlusion. As indicated in FIG. 1, longitudinal member 100a serves as an antegrade member and longitudinal member 100b serves as a retrograde member. An RF generator 10 (also referred to as a controller) serves as the source of RF energy to be provided to longitudinal members 100a and 100b. Longitudinal members 100a and 100b may be guidewires, catheters, micro-catheters, or dilating catheters. In a preferred embodiment, longitudinal members 100a and 100b are guidewires. Thus, while in the following description the term "guidewire" is used to refer to a longitudinal member 100a or 100b, it is understood that the term "guidewire" as used herein is intended to include any other type of longitudinal member.

To provide RF energy from the RF generator 10 to the guidewires 100a and 100b, a pigtail 20 connects at its proximal end to the RF generator 10 and terminates at its distal end in a connector 30. Connector 30 is a standard connector that couples the input and output signals of the RF generator 10 to the guidewires 100a and 100b.

Guidewires 100a and 100b are configured to have sufficient torsional rigidity and longitudinal flexibility to advance through an occlusion, and to align their electrodes in a direction away from the vessel wall, towards the other longitudinal member, or any combination thereof.

Figure 2:
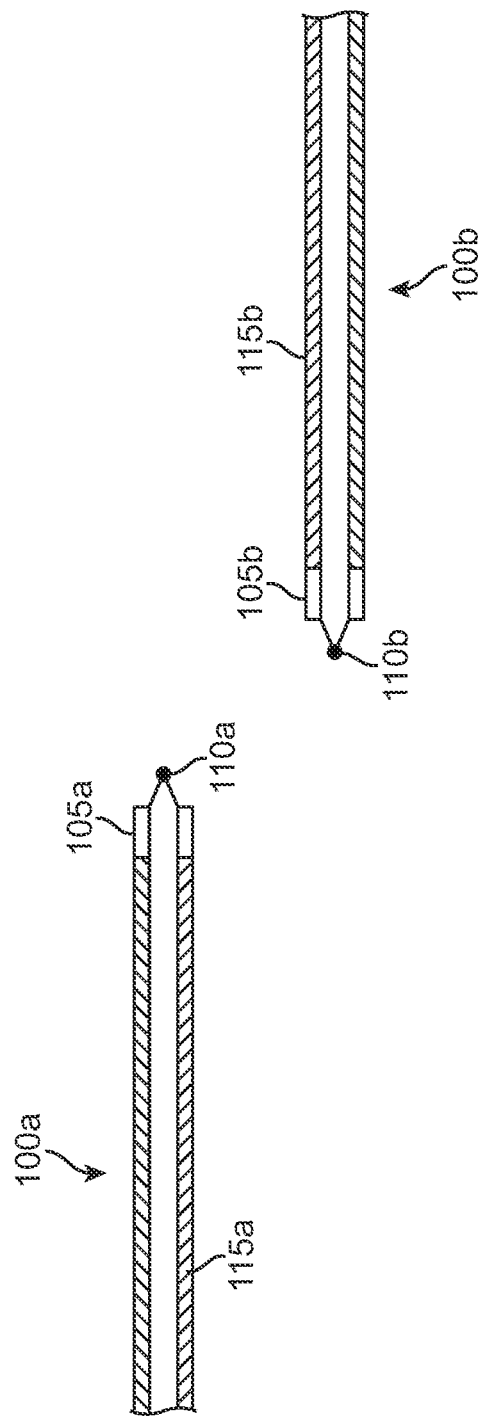
FIG. 2 shows the features of the longitudinal members.

As shown in FIG. 2, the antegrade and retrograde guidewires 100a and 100b have conductive electrodes 105a and 105b, respectively, at their distal ends. In one embodiment, the electrodes 105a and 105b are located on one side of their respective guidewires 100a and 100b, thereby providing the operating physician with the freedom to allow the electrode-free side of the guidewire to touch the vessel wall (if needed) while still directing the RF energy away from the vessel wall. Additionally, this allows the configuration to direct the RF energy away from the vessel wall, thereby minimizing potential RF injury to the vessel wall. In one embodiment, one or more of the guidewires comprises a plurality of electrodes arranged in an array.

Conductive wires (not shown) connect the electrodes 105a and 105b to connector 30 to deliver RF energy from the RF generator 10 to the electrodes 105a and 105b. The exterior of the guidewires are covered by non-conductive layers 115a and 115b, respectively, that sandwich the conductive wires between the guidewires and the non-conductive layers. In one embodiment, the non-conductive layers 115a and 115b comprise a sheath or coating.

In one embodiment, and as further shown in FIG. 2, the guidewires 100a and 100b comprise temperature measuring elements 110a and 110b at the distal tip of the antegrade and retrograde guidewires, respectively. In one embodiment, the temperature measuring elements 110a and 110b comprise thermocouples or thermistors that are connected to the connector 30. In another embodiment, pressure measuring elements are placed on the distal ends of the guidewires to detect a change in pressure upon activation of the RF energy.

RF generator 10 is configured to allow the user to set a maximum temperature, a treatment time period, a level of RF power, or a combination of these control parameters. The treatment time period indicates the period of time over which the RF energy will flow between the electrodes. The maximum temperature setting serves as a threshold temperature for the tissue that is in contact with the electrodes, and the RF generator 10 can be set to reduce or shut off power to one or both electrodes when one or more of the temperature measuring elements 110a and 110b indicate a tissue temperature at or near the threshold.

In one embodiment, the generator 10 is capable of measuring the impedance of the tissue between the two electrodes 105a and 105b. Based on the type of the occlusion (i.e., the nature of the calcified material), the user can choose the appropriate combination of temperature, treatment time, and the amount of RF energy to be provided to the tissue to achieve a safe and effective treatment. Alternatively, the treatment may proceed with the user manually controlling the parameters during the recanalization procedure, with the user treating the occlusion until recanalization is achieved.

Figure 3A:
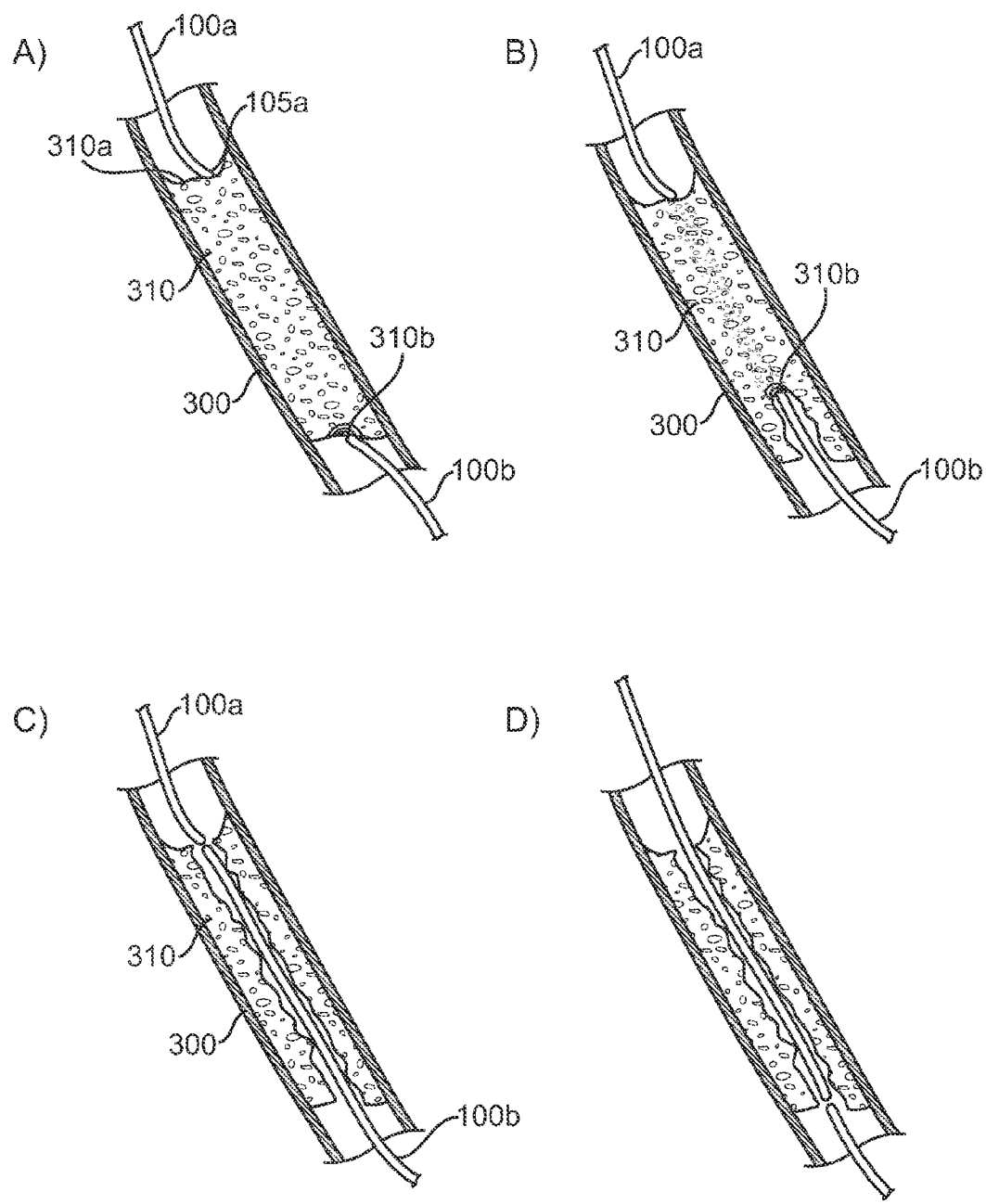
FIGS. 3A and 3B show the steps involved in recanalizing a CTO using bipolar RF and combined antegrade and retrograde approach.
Figure 3B:
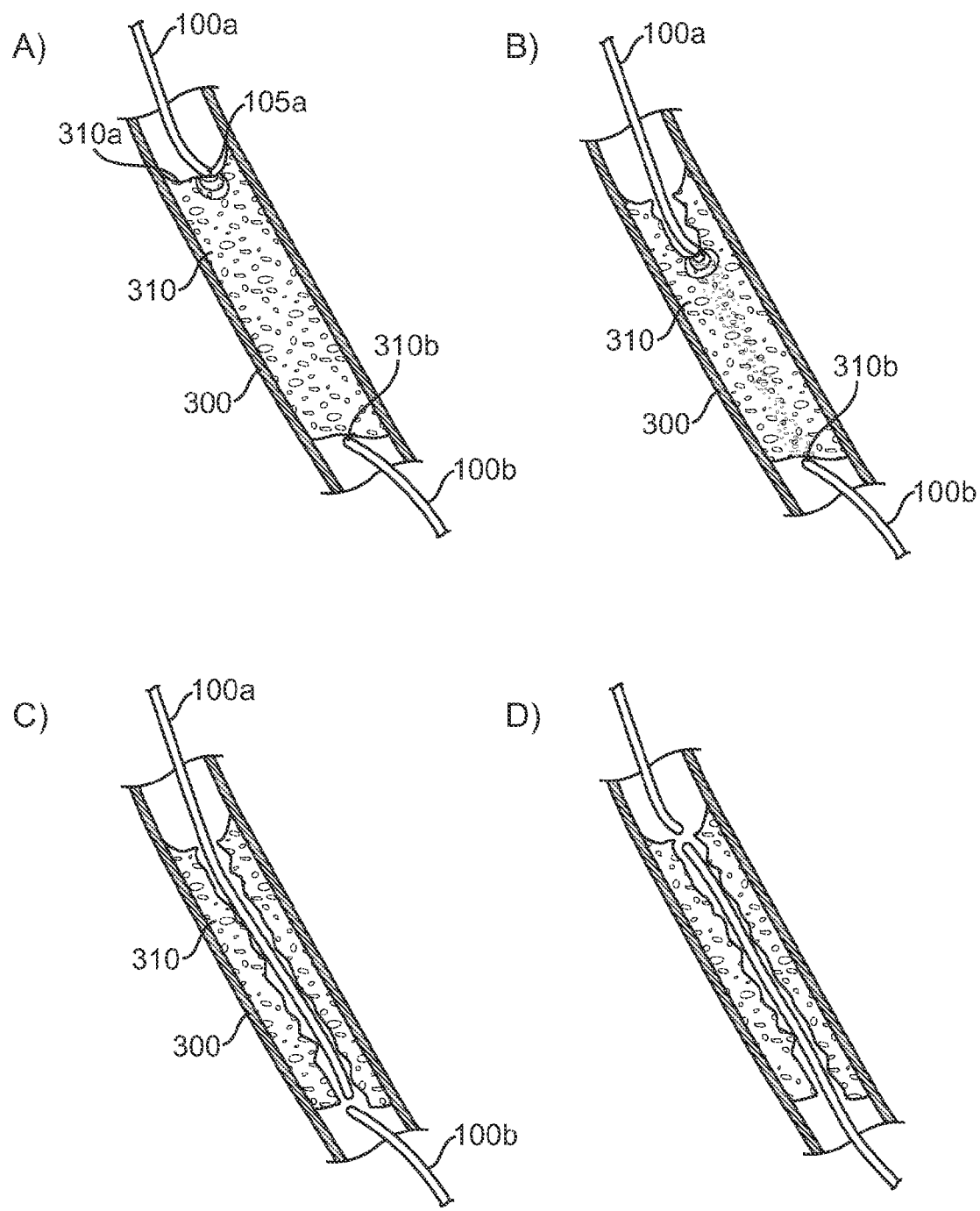

The sequence of the recanalization treatment steps are illustrated in FIGS. 3A and 3B. As shown in diagram A of FIG. 3A, the antegrade guidewire 100a and retrograde guidewire 100b are advanced to the proximal and distal ends 310a and 310b of the occlusion 310, respectively. This can be accomplished using standard angioplasty techniques. As described in the above referenced co-pending U.S. patent application Ser. No. 11/706,041, the retrograde guidewire can be advanced to the distal end of the occlusion 310b using collaterals such as the septals.

Once the user has confirmed that the guidewires 100a and 100b are in contact with the occlusion 310 and are not touching the vessel wall 300, the RF treatment is initiated. Alternatively, the guidewires are advanced as deep into the occlusion as possible to minimize the distance between the electrodes and, consequently, minimize the length of the ablation zone. Confirmation that the guidewires 100a and 100b are in an appropriate position can be generated by impedance measurements and/or by using any of the standard imaging techniques employed during interventional procedures, such as fluoroscopy or intravascular ultrasound (IVUS), in which transducers are placed on the distal ends of the guidewire. When using tissue impedance measurements, the calcified occlusion 310 generally exhibits significantly higher impedance than the vessel wall 300. If an impedance measurement indicates a low impedance value, it is likely that one or both guidewires are in contact with the vessel wall 300, and appropriate repositioning of the guidewires may be warranted.

Upon initiating the recanalization RF treatment, the occlusion 310 is ablated from the ends 310a and 310b of the occlusion 310 to the interior of the occlusion 310, as shown in FIG. 3A diagram B. The user then slowly and carefully advances one or both guidewires 100a and 100b until a channel or path is created in the occlusion 310, as shown in FIG. 3A diagram C. As shown in FIG. 3A, the antegrade guidewire 100a may be kept stationary and the retrograde guidewire 100b may be advanced through the occlusion 310. Once a channel has been created, the retrograde guidewire 100b may be withdrawn and the antegrade guidewire 100a may be advanced through the occlusion 310, as shown in FIG. 3A diagram D, and standard interventional procedures, such as balloon angioplasty, can be performed. Alternatively, the retrograde guidewire 100b can be kept stationary during the RF treatment and the antegrade guidewire 100a can be advanced through the occlusion 310. This is illustrated in FIG. 3B diagrams A-D.

Figure 4:
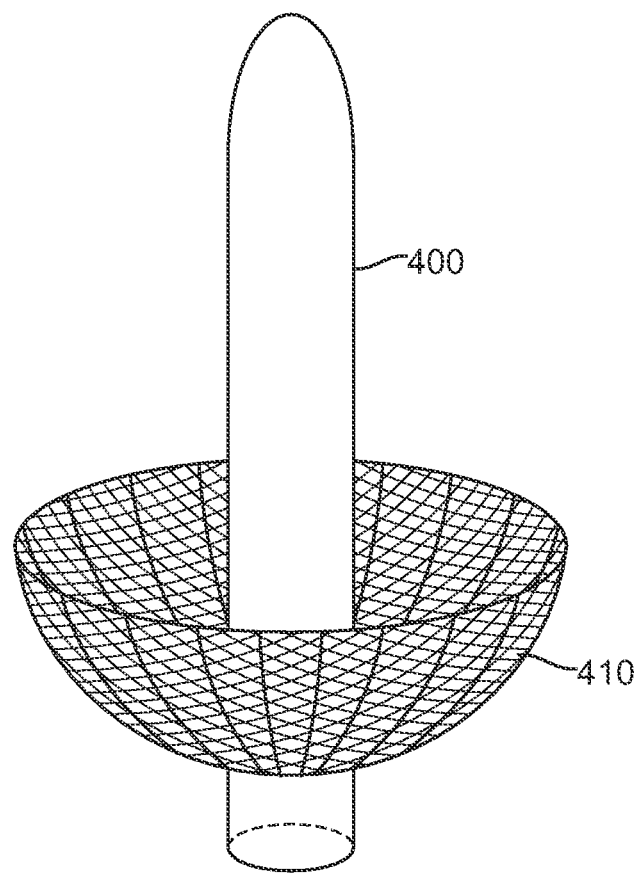
FIG. 4 shows an example embodiment of a longitudinal member comprising an embolic protection mechanism.

Optionally, the catheter comprises a means for removing or withdrawing debris resulting from the RE ablation. For example, a mechanism could be provided to capture and retrieve the debris, or a suction device could be provided to actively remove the debris near the ablation area. Examples of such embolic protection mechanisms are disclosed in the above referenced co-pending U.S. patent application Ser. No. 11/706,041. FIG. 4 shows an example embodiment of a longitudinal member 400 comprising an embolic protection mechanism 410. The embolic protection mechanism 410 comprises filter, mesh, net, or similar element, for capturing and retrieving ablation debris. As another example, the embolic protection may comprise a balloon for occluding the vessel and preventing the debris from circulating, and for subsequent aspiration of the debris through a longitudinal member. As another example, if a sheath is provided, such sheath may also be configured to be or to include a debris capture and retrieval mechanism or a suction device. In one embodiment, a longitudinal member may be retracted, and the remaining sheath may be used as a capture and retrieval mechanism or a suction device to remove ablation debris. In another embodiment, the longitudinal member comprises an ablating wire housed in the lumen of a dilating catheter. Upon ablation, the ablating wire may be retracted and the dilating catheter may be used to remove the debris. Alternatively, the system comprises a separate catheter to provide suction, or otherwise capture and remove the debris from the ablation site.

Optionally, the device may be coupled to an electrocardiogram (EKG) machine to aid in timing energy emissions. For example, the rate of blood flow through the coronary arteries typically varies during the cardiac cycle. During systole when the heart is contracting, flow through the arteries is generally lower than during diastole. In one embodiment, energy emission is timed during diastole, for example using an algorithm to detect the R-wave of an EKG, and energy emission is timed to occur when flow is highest, thereby maximizing the cooling effect provided by blood flow and consequently minimizing the heat exposure to the vessel. Additionally, coronary artery dimensions can vary during the cardiac cycle and energy emission can similarly be timed to take advantage of this fact.

Optionally, the device comprises a mechanism for detecting or estimating the distance between the electrodes, and for decreasing the amount of delivered RF energy as the distance between the electrodes decreases, thereby minimizing potential RF injury to the vessel wall.

Figure 5A:
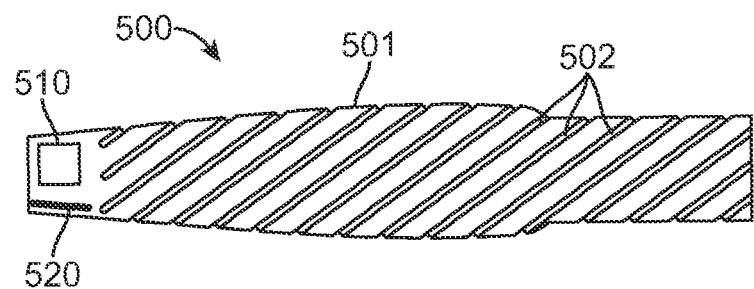
FIGS. 5A-C show a longitudinal member structurally configured along at least part of the length of the catheter to enable advancement or alignment of the longitudinal member through a narrow diameter blood vessel or occlusion.
Figure 5B:
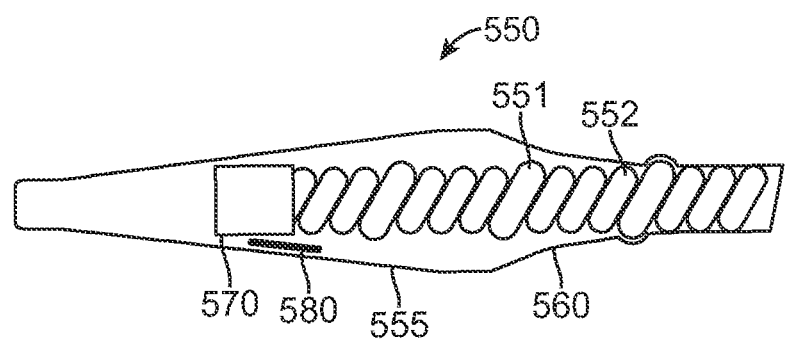
Figure 5C:
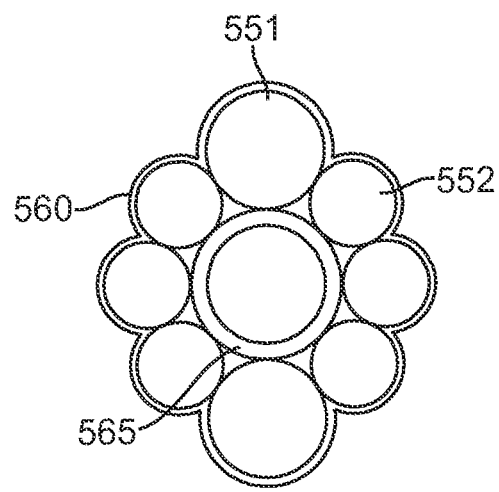

In another embodiment, the device is an ablation catheter comprising a longitudinal member having a distal end, a proximal end, and a guidewire shaft there-between comprising a guidewire lumen. The longitudinal member is a dilating catheter and is structurally configured along at least part of the length of the catheter to enable advancement or alignment of the longitudinal member through a narrow diameter blood vessel or occlusion. Advancement is achieved, for example, by turning or twisting the longitudinal member. FIGS. 5A-5C show such an embodiment of the present invention. For example, as shown in FIG. 5A, the longitudinal member 500 may comprise a helical exterior 501 that advances through the vessel and dilates the vessel as the member is being twisted or rotated. Helical exterior 501 comprises a plurality of grooves 502 carved into the outer body of the longitudinal member 500. The distal tip of longitudinal member 500 optionally comprises a radiopaque marker 510. An electrode 520 is located at or near the distal end of the catheter. Another example is shown in FIG. 5B, the cross section of which is shown in FIG. 5C. The longitudinal member 550 may comprise a plurality of wires 551 and 552 wound around a liner 565 within tip 555. Tip 555 is narrowest at the distal tip of the device. In one embodiment, the wires 551 and 552 comprise at least two different diameters. Longitudinal member 550 optionally terminates at a marker 570. An electrode 580 is located at or near the distal end of the longitudinal member 550. The ablation catheter additionally and optionally comprises conductive wires for transmitting energy between the electrode and an external energy source. Alternatively, the plurality of wires may be configured to act as the electrode or conductive wires. Additionally and optionally, the catheter comprises an insulating sheath 560 which is optionally retractable.

The guidewires and electrodes may be made from any one or more suitable materials as is commonly known in the art. Examples of such suitable materials include stainless steel, Nitinol, Elgiloy, platinum, iridium, tantalum, titanium, cobalt, chromium, or any combinations thereof. In one embodiment, one or more of the guidewires may be made of a polymer, with an electrically conductive core for transmitting electrical energy to the respective electrodes.

While the above embodiments refer to the use of RF energy for the purpose of ablation, it should be noted that other energy modalities may be used as well, for example ultrasound energy. In one embodiment, one or more longitudinal members of the recanalization systems of the present invention comprise one or more ultrasound transducers, instead of or in addition to RF electrodes. The ultrasound transducers provide ultrasound energy for ablating an occlusion. In one embodiment, both the antegrade and the retrograde longitudinal members comprise ultrasound transducers and ablate the lesion from an antegrade as well as a retrograde direction. Other energy modalities could include microwave and laser.

It should be noted that the combined antegrade and retrograde energy delivery techniques described above could also be used as an adjunct technique to crossing CTOs in combination with using conventional methods. The technique could be used to sufficiently soften or weaken the occlusion, thereby allowing a guidewire or catheter to cross the occlusion.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A method of recanalizing an occluded vessel, comprising:
    advancing in an antegrade fashion a first longitudinal member to a proximal end of an occlusion;
    advancing in an retrograde fashion a second longitudinal member to a distal end of an occlusion;
    ablating the occlusion by applying energy, from an energy source coupled to the first longitudinal member and the second longitudinal member, between the first and second longitudinal members, wherein the applying comprises applying energy from at least one of the first longitudinal member or the second longitudinal member; and
    recanalizing the occlusion.

2. The method of claim 1, wherein the energy is radiofrequency energy.

3. The method of claim 1, wherein the energy is laser energy.

4. The method of claim 1, wherein the energy is microwave energy.

5. The method of claim 1, wherein the energy is ultrasound energy.

6. The method of claim 1, further comprising:
    timing the applying with an electrocardiogram (EKG) signal.

7. The method of claim 6, wherein the timing comprises detecting an R-wave of the electrocardiogram (EKG) signal.

8. The method of claim 1, further comprising:
    capturing and retrieving debris.

9. A method of recanalizing an occluded vessel, comprising:

advancing in an antegrade fashion a first longitudinal member to a proximal end of an occlusion;

advancing in a retrograde fashion a second longitudinal member to a distal end of the occlusion;

applying energy between the first and second longitudinal members, wherein the applying is timed to occur when blood flow is highest, thereby maximizing the cooling effect of blood flow and minimizing heat exposure to the vessel; and recanalizing the occlusion.

* * * * *